US011849993B2

(12) United States Patent
Miller et al.

(10) Patent No.: US 11,849,993 B2
(45) Date of Patent: Dec. 26, 2023

(54) ELECTROSURGICAL DEVICE WITH VACUUM PORT HAVING MULTIPLE SWIVEL CONNECTIONS

(71) Applicant: Buffalo Filter LLC, Lancaster, NY (US)

(72) Inventors: Michael J. Miller, Depew, NY (US); Timothy Hersey, Tonawanda, NY (US); Samantha Bonano, Williamsville, NY (US); Kyrylo Shvetsov, Depew, NY (US)

(73) Assignee: Buffalo Filter LLC, Lancaster, NY (US)

( * ) Notice: Subject to any disclaimer, the term of this patent is extended or adjusted under 35 U.S.C. 154(b) by 462 days.

(21) Appl. No.: 15/665,859

(22) Filed: Aug. 1, 2017

(65) Prior Publication Data

US 2018/0028255 A1    Feb. 1, 2018

Related U.S. Application Data

(60) Provisional application No. 62/369,625, filed on Aug. 1, 2016.

(51) Int. Cl.
*A61B 18/12* (2006.01)
*A61B 18/14* (2006.01)
*A61B 18/00* (2006.01)

(52) U.S. Cl.
CPC .......... *A61B 18/12* (2013.01); *A61B 18/1402* (2013.01); *A61B 2018/00696* (2013.01); *A61B 2218/008* (2013.01)

(58) Field of Classification Search
CPC ................ A61B 18/12; A61B 18/1402; A61B 2218/008; A61B 2018/00696;
(Continued)

(56) References Cited

U.S. PATENT DOCUMENTS 4,911,159 A * 3/1990 Johnson ............. A61B 18/1402
606/37
5,674,219 A    10/1997 Monson et al.
(Continued)

OTHER PUBLICATIONS

International Search Report for corresponding PCT Application PCT/US2017/044927 dated Oct. 6, 2017, dated Sep. 22, 2017.

*Primary Examiner* — Joseph A Stoklosa
*Assistant Examiner* — Adam J Avigan
(74) *Attorney, Agent, or Firm* — Timothy W. Menasco, Esq.; Harter Secrest & Emery LLP (57) ABSTRACT

Presented are a method and apparatus for surgical procedures. An exemplary apparatus includes a body having a longitudinal axis, the body comprising a hollow passageway extending through the longitudinal axis from an inlet at a distal end to a port at a proximal end. The apparatus further includes an electrode extending from the distal end of the body adjacent to the inlet. The apparatus also includes a swivel portion moveably coupled to the port, the swivel portion having a second hollow passageway fluidly coupled to the hollow conduit extending from the port to an outlet, wherein the swivel portion comprises a first swivel element operable to rotate around the longitudinal axis relative to the body, and wherein the swivel portion comprises a second swivel element operable to rotate relative to the first swivel element and the body.

12 Claims, 11 Drawing Sheets

(58) Field of Classification Search
CPC ........... A61B 2018/00202; A61B 2018/00053; A61B 2018/00184; A61B 2018/00172; A61B 2018/0091; A61B 2018/00291; A61B 2218/007; A61B 18/1492; A61B 2217/005

See application file for complete search history.

(56) References Cited

U.S. PATENT DOCUMENTS

| | | |
|---|---|---|
| 8,414,576 B2 | 4/2013 | Cosmescu |
| 2001/0051804 A1 | 12/2001 | Mulier et al. |
| 2002/0019631 A1 | 2/2002 | Kidder et al. |
| 2005/0107782 A1 | 5/2005 | Reschke |
| 2009/0018539 A1* | 1/2009 | Cosmescu ......... A61M 39/1055 606/41 |
| 2011/0190768 A1 | 8/2011 | Shvetsov et al. |
| 2012/0310229 A1 | 12/2012 | Gregg |
| 2015/0209100 A1 | 7/2015 | Ineson |
| 2015/0257816 A1 | 9/2015 | Ineson |
| 2015/0306348 A1 | 10/2015 | Wallace et al. |
| 2016/0175033 A1 | 6/2016 | Le |
| 2017/0014559 A1* | 1/2017 | Minskoff ............ A61M 1/0027 |

* cited by examiner

ELECTROSURGICAL DEVICE WITH VACUUM PORT HAVING MULTIPLE SWIVEL CONNECTIONS

BACKGROUND OF THE INVENTION

Field of the Invention

The present invention relates generally to smoke evacuation and more specifically to an electrosurgical device with smoke evacuation during medical procedures.

Description of Related Art

Surgical smoke and aerosol, or plume, is created in connection with surgery. For example, when laser or electrosurgical energy is delivered to a cell, heat is created. This heat vaporizes the intracellular fluid, which increases the pressure inside the cell and eventually causes the cell membrane to burst. In this example, a plume of smoke containing water vapor is released into the atmosphere of the operating room or doctor's office. At the same time, the heat created may char the protein and other organic matter within the cell, and may cause thermal necrosis in adjacent cells. The charring of cells may also release other harmful contaminants, such as carbonized cell fragments and gaseous hydrocarbons.

BRIEF SUMMARY OF THE INVENTION

In view of the foregoing, it is an object of the present disclosure to provide an apparatus, electrosurgical device and method for surgical procedures.

A first exemplary embodiment of the present disclosure provides an apparatus for surgical procedures. The apparatus includes a body having a longitudinal axis, the body including a hollow passageway extending through the longitudinal axis from an inlet to a port. The apparatus further includes a swivel portion moveably coupled to the port, the swivel portion having a second hollow passageway fluidly coupled to the hollow passageway extending from the port to an outlet, wherein the swivel portion is operable to rotate around the longitudinal axis relative to the body, and wherein the swivel portion comprises a hollow socket and a hollow ball, the hollow ball operable to rotate within the socket relative to the socket.

A second exemplary embodiment of the present disclosure provides electrosurgical device. The electrosurgical device includes a body having a longitudinal axis, the body comprising a hollow passageway extending through the longitudinal axis from an inlet at a distal end to a port at a proximal end, and an electrode extending from the distal end of the body adjacent to the inlet. The electrosurgical device further includes a swivel portion moveably coupled to the port, the swivel portion having a second hollow passageway fluidly coupled to the hollow passageway extending from the port to an outlet, wherein the swivel portion comprises a first swivel element operable to rotate around the longitudinal axis relative to the body, and wherein the swivel portion comprises a second swivel element operable to rotate relative to the first swivel element and the body.

A third exemplary embodiment of the present disclosure provides a method. The method includes providing a body having a longitudinal axis, the body comprising a hollow passageway extending through the longitudinal axis from an inlet at a distal end to a port at a proximal end, and providing an electrode extending from the distal end of the body adjacent to the inlet. The method further includes providing a swivel portion moveably coupled to the port, the swivel portion having a second hollow passageway fluidly coupled to the hollow passageway extending from the port to an outlet, wherein the swivel portion comprises a first swivel element operable to rotate around the longitudinal axis relative to the body, and wherein the swivel portion comprises a second swivel element operable to rotate relative to the first swivel element and the body.

The following will describe embodiments of the present invention, but it should be appreciated that the present disclosure is not limited to the described embodiments and various modifications of the invention are possible without departing from the basic principles. The scope of the present disclosure is therefore to be determined solely by the appended claims.

DETAILED DESCRIPTION OF THE INVENTION

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Figure 1:
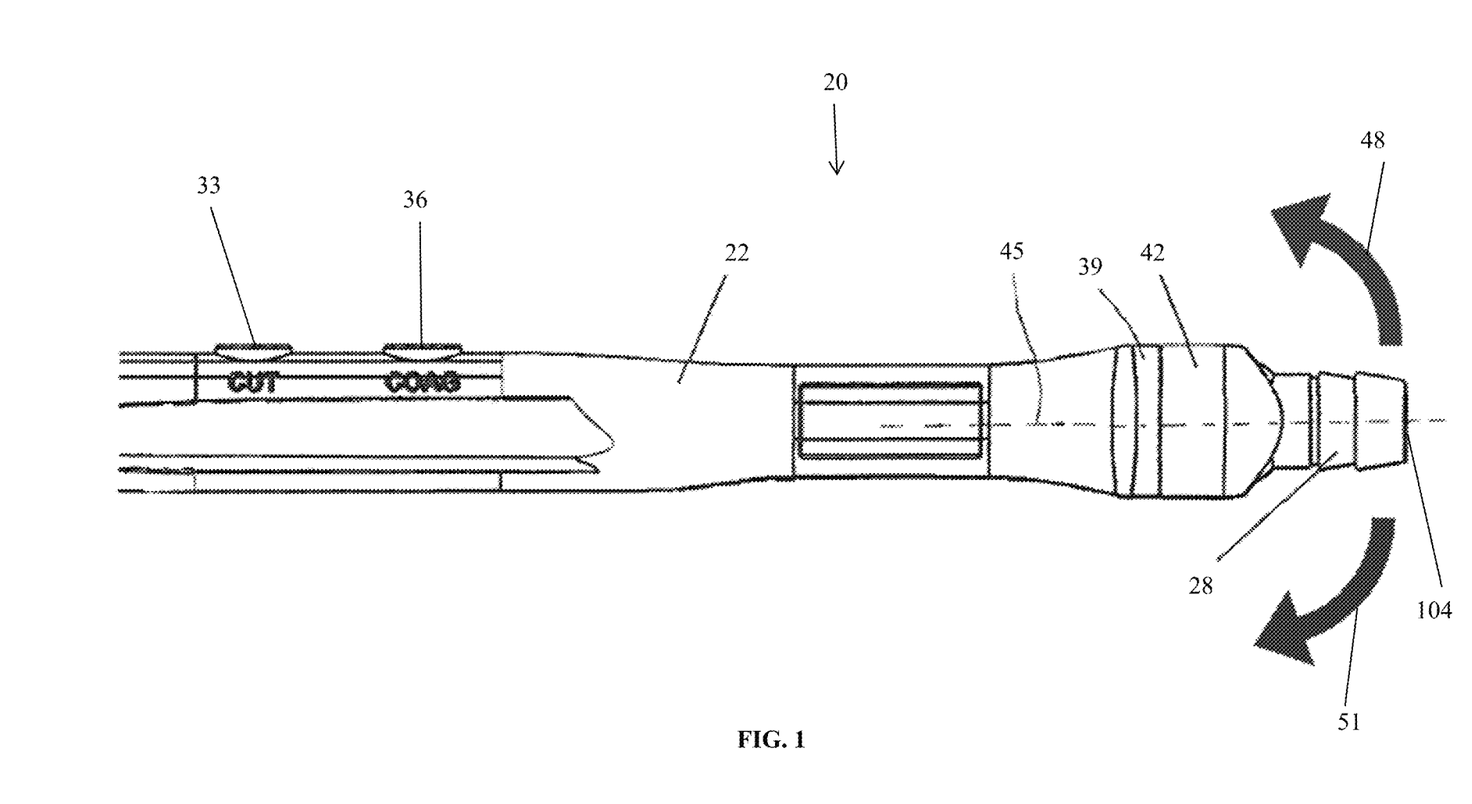
FIG. 1 is a side elevation view of a device suitable for use in practicing exemplary embodiments of this disclosure.

Referring now to the drawings, and more particularly to FIG. 1 thereof, this invention provides an electrosurgical device having a vacuum port, generally indicated at 20, which is particularly adapted for (but not limited to) suctioning smoke during electrosurgery.

Shown in FIG. 1 is the proximal end of an electrosurgical device 20 having a longitudinal axis 45. The electrosurgical device 20 includes a hollow body 22 enclosing a passageway 302 (shown in FIG. 3) extending through the longitudinal axis 45 from a distal end 1104 (shown in FIG. 11) holding an electrode 1100 to a proximal end 39 having a port 306. The proximal end 39 and port 306 of the body 22 is disposed adjacent to a swivel portion 42 having a barbed fitting 28 for attachment to a conduit such as a vacuum tube 202 or plastic hose leading to the vacuum power unit 204 (shown in FIG. 2). Port 306, passageway 302, outlet 104, and passageway 304 are fluidly connected. A conduit 202 (shown in FIG. 2) may extend from a vacuum power unit 204 to the barbed fitting 28 at the end of the electrosurgical device 20 operable for removing the surgical smoke through the body 22 and passageway 302 of the electrosurgical device 20 and through vacuum tube 202. The distal end 1104 of the electrosurgical device 20 (shown in FIG. 11) may be provided with an inlet 1102 to passageway 302. The smoke generated by the electrosurgical device 20 enters the inlet 1102 which is in fluid communication with a passageway 302 through the body 22 of the electrosurgical device 20. The passageway 302 is disposed in fluid communication with swivel portion 42 having a hollow passageway 304 and an outlet 104 of the electrosurgical device 22 where the barbed fitting 28 is located. Accordingly, smoke and debris from the procedure may be conveyed from the inlet 1102 through the electrosurgical device 20 and hollow passageway 304 of swivel portion 42 to the outlet 104 of the electrosurgical device 20 surrounded by the barbed fitting 28. From the outlet 104, the smoke and debris is conveyed through a conduit 202 toward the vacuum source 204. It is further noted that barbed fitting 28 does not have to be a barbed fitting 28, and that any male or female connection can be substituted. For example, a female connector may be used in place of barbed fitting 28 so as to keep the inner diameter of the fitting, and hence the passageway 304 (see FIG. 3), as large as possible.

Figure 3:
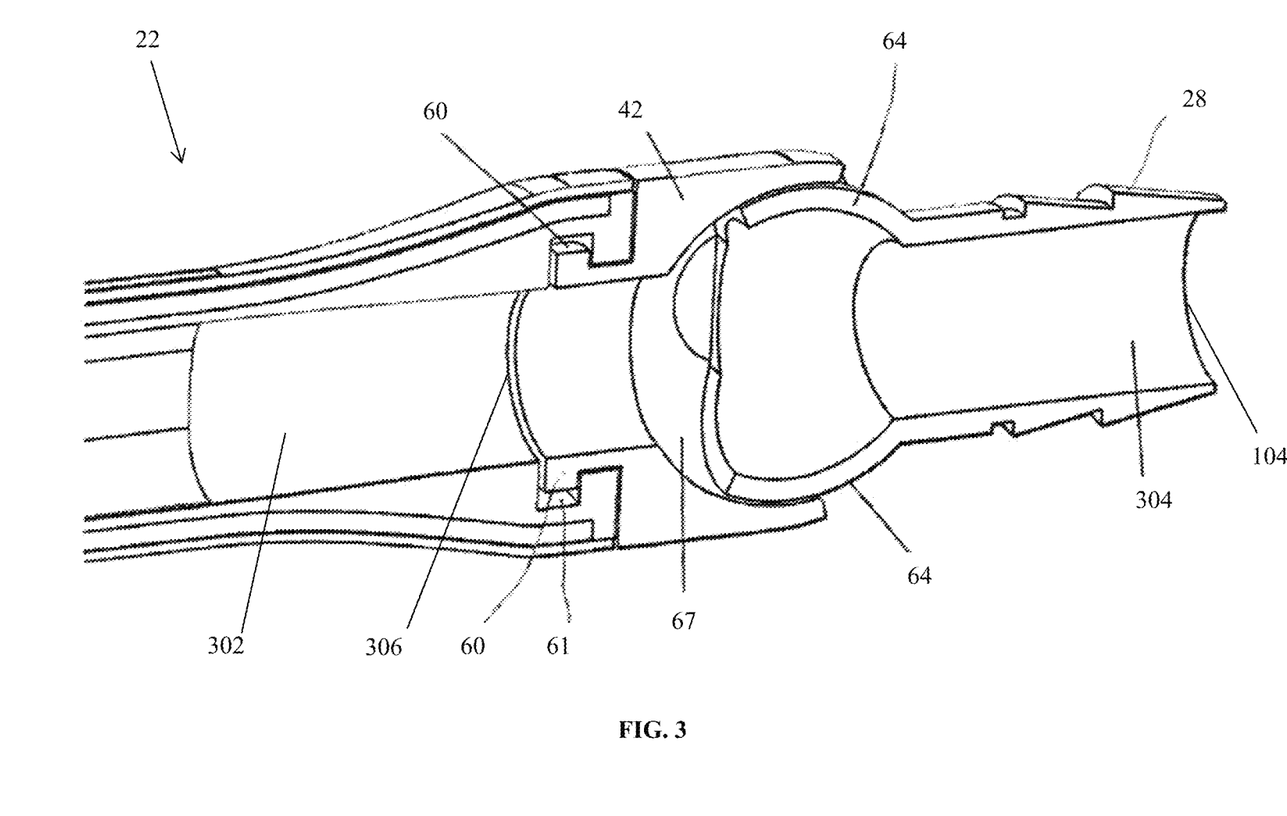
FIG. 3 is a partial perspective cross-sectional view of a device suitable for use in practicing exemplary embodiments of this disclosure.
Figure 11:
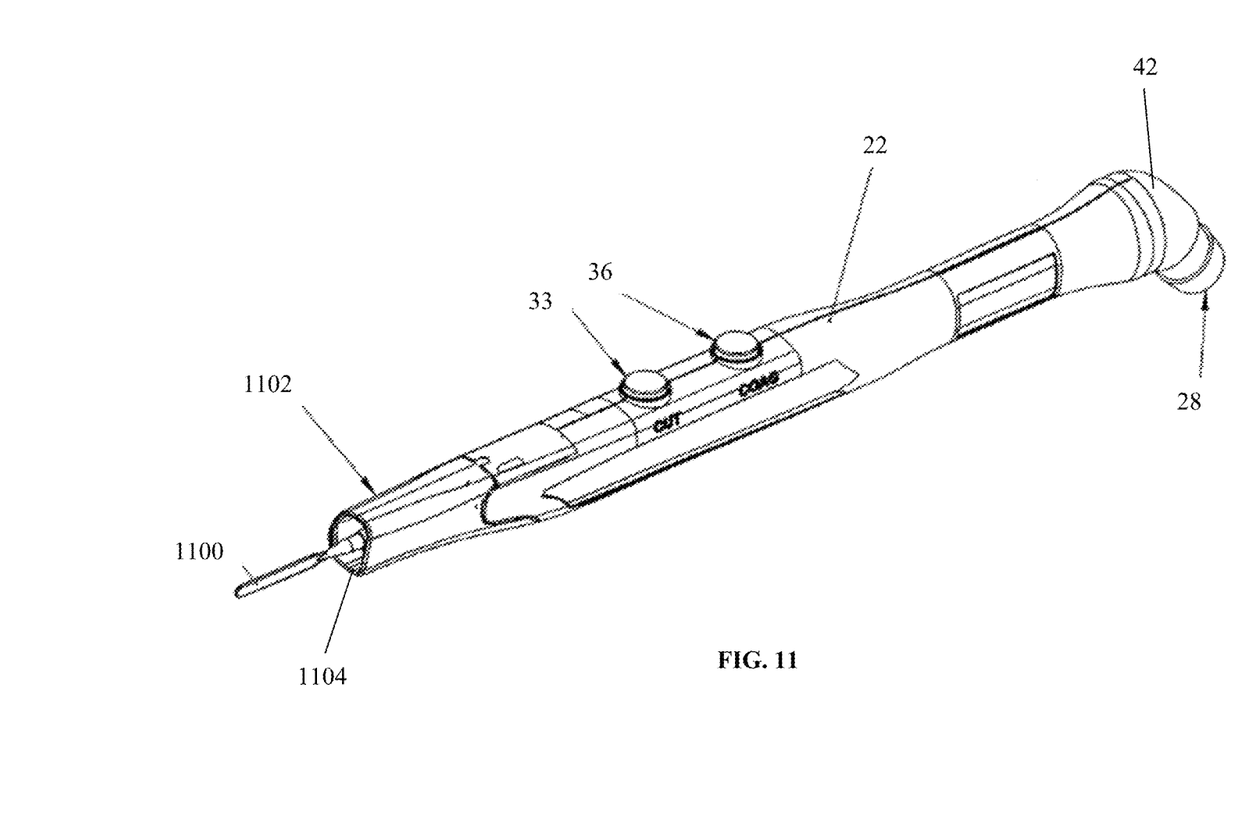
FIG. 11 is a perspective view of an electrosurgical device suitable for use in practicing exemplary embodiments of this disclosure.

As shown, the electrosurgical device 20 may be provided with a cut button 33 and a coagulate button 36 that provide different levels of current to the electrode 1100 at the distal end 1104 of the electrosurgical device 20. In one embodiment, the cut button 33 is operable to activate the electrode 1100 at a first power level and coagulate button 36 is operable to activate the electrode 1100 at a second power level. The first power level in embodiments is different from the second power level. The proximal end 39 of the body 22 is disposed adjacent to a swivel portion 42. The swivel portion 42 is connected to the body 22 but is configured and arranged to rotate about the longitudinal axis 45 of the electrosurgical device 20. The rotatable connection between the swivel portion 42 and the body 22 is shown in FIG. 3. Returning to FIG. 1, the barbed fitting 28 may be pivotally attached to the swivel portion 42 such that the barbed fitting may rotate relative to the swivel portion 42 which in turn may rotate relative to the body 22. Accordingly, the system provides significant flexibility with regard to the positioning of the conduit 202 leading to the vacuum unit 204. As indicated by arrows 48 and 51, the barbed fitting 28 can be rotated upward or downward with respect to the orientation shown in FIG. 1.

Figure 2:
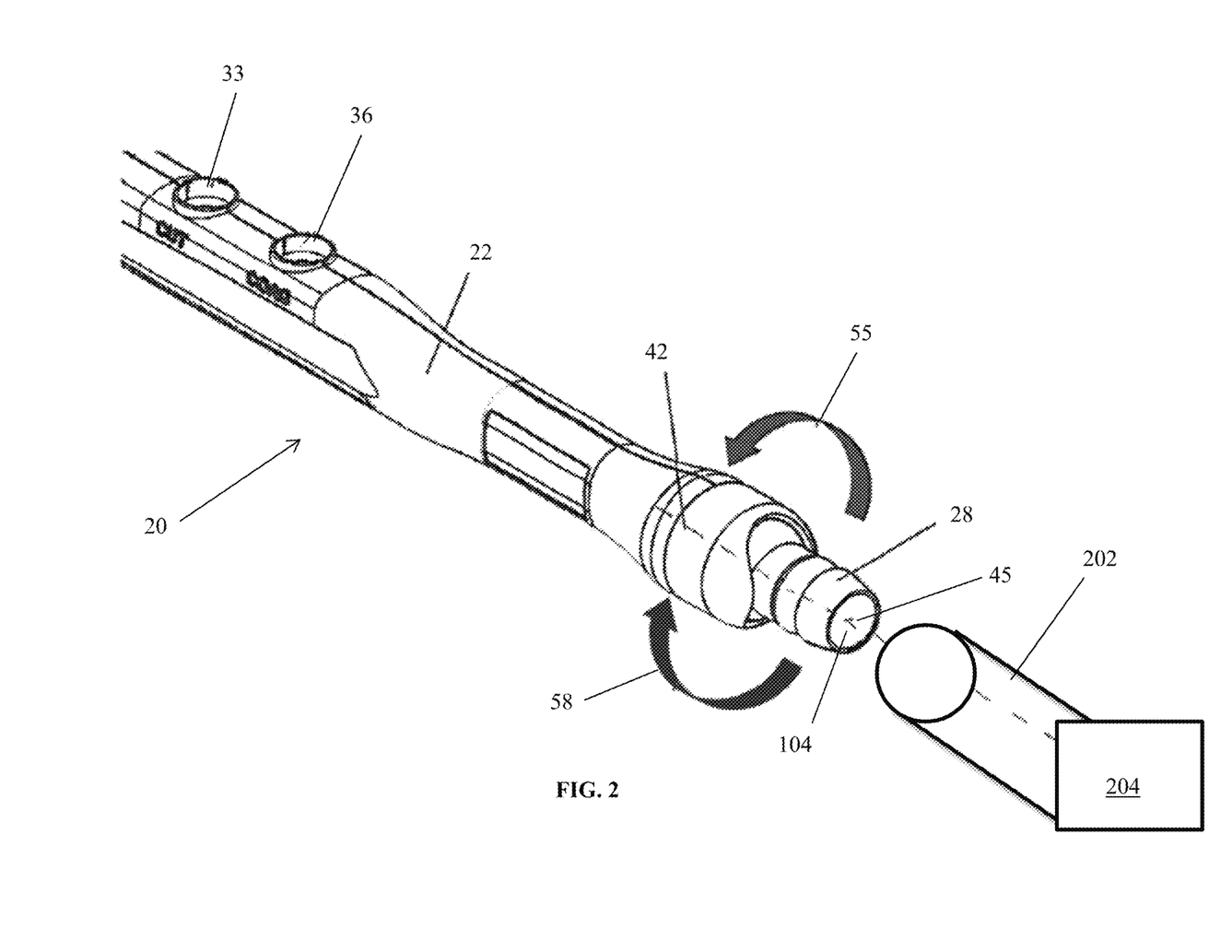
FIG. 2 is a perspective view of a device suitable for use in practicing exemplary embodiments of this disclosure.

Turning to FIG. 2, as described above the swivel portion 42 is configured and arranged to rotate freely in either direction about the longitudinal axis 45 of the electrosurgical device 20 in the direction of arrows 55 and 58.

As shown in FIG. 3, the swivel portion 42 has a ring portion 60 that rotates inside a slot 61 defined in the inner wall of the body 22. The engagement of the ring portion 60 with the slot 61 provides for rotation of the swivel portion 42 relative to the body 22 and also prevents the swivel portion 42 from disconnecting from the body 22.

The barbed fitting 28 includes passageway 304 to provide an air pathway to the conduit 202 that is attached to the outlet 104. The barbed fitting 28 is connected to a ball 64 that fits inside a socket 67 formed in the end of the swivel portion 42. Accordingly, the barbed fitting 28 may be pivoted and rotated in many different directions in the ball and socket configuration.

Figure 4A:
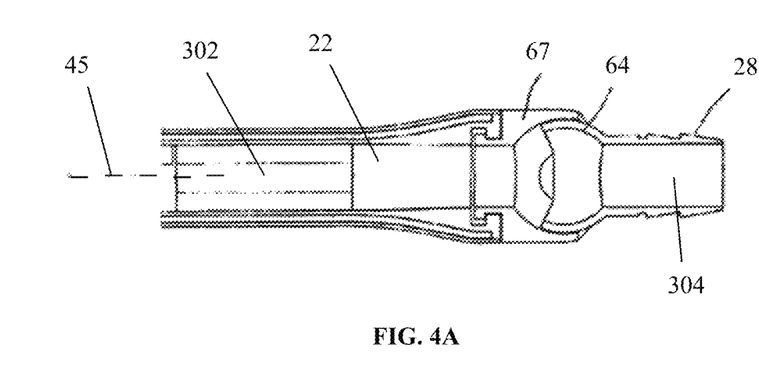
FIG. 4A is a partial side cross-sectional view of a device suitable for use in practicing exemplary embodiments of this disclosure.
Figure 4B:
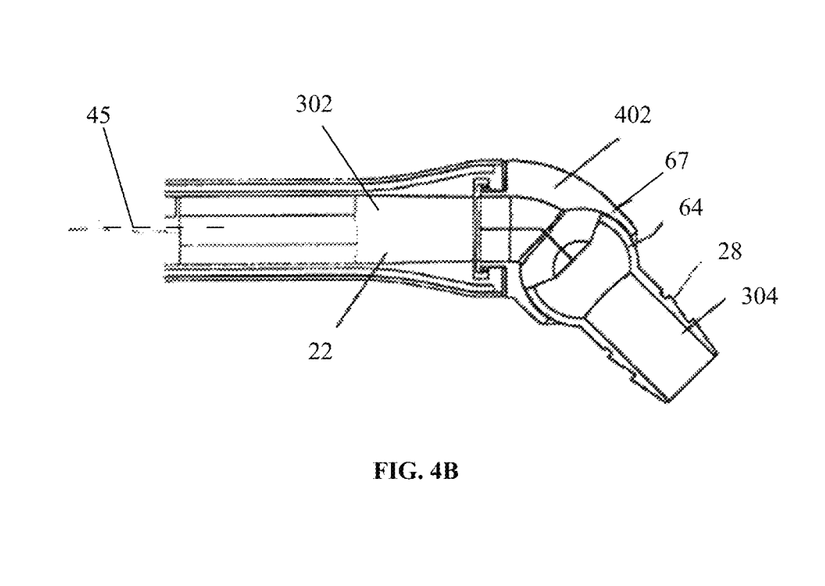
FIG. 4B is a partial side cross-sectional view of an alternative embodiment of a device suitable for use in practicing exemplary embodiments of this disclosure.

Turning to FIGS. 4A and 4B, the barbed fitting 28 may be connected to the swivel portion 42 in the direction of the longitudinal axis 45 as shown in FIG. 4A. Alternatively and in order to provide a greater range in movement of the swivel assembly, the swivel portion 42 may be angled along a side 402 as shown in FIG. 4B. Accordingly, the barbed fitting 28 is connected at an angle relative to the longitudinal axis 45 of the electrosurgical device 20. Embodiments of angled side 402 create an angle between 0 degrees to 90 degrees relative to the longitudinal axis 45.

Figure 5:
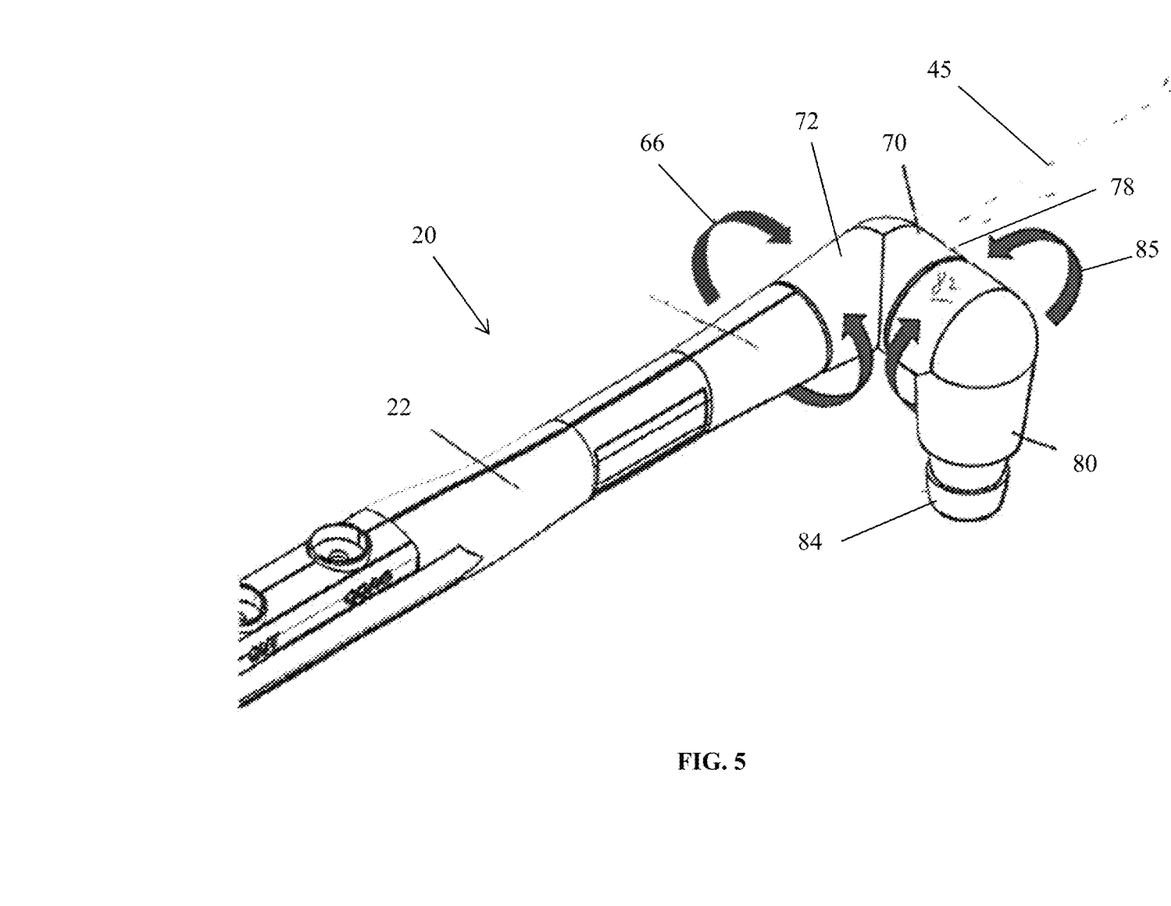
FIG. 5 is a perspective view of a second embodiment of a device suitable for use in practicing exemplary embodiments of this disclosure.

In another embodiment shown in FIG. 5, a swivel portion 70 may be angled at approximately ninety degrees. However, it should be appreciated that embodiments of swivel portion 70 include being angled between 0 degrees to 90 degrees. As shown in FIG. 5, the body 22 connects with a first end 72 of the swivel portion 70. The first end 72 rotates about the longitudinal axis 45 in the direction of arrow 66. The second end 78 of the swivel portion 70 may be disposed at an approximately ninety degree angle with respect to the first end 72. However, embodiments include the second end 78 of swivel portion 70 being disposed anywhere between approximately 0 degrees to 90 degrees. The hose connector 80 may also be angled at approximately ninety degrees between a first end 82 and a second end 84. Embodiments include the hose connector 80 being angled anywhere between approximately 0 degrees to 90 degrees. The first end 82 of the hose connector 80 is capable of rotating relative to the second end 78 of the swivel portion 70 in the direction of arrow 85.

Figure 6:
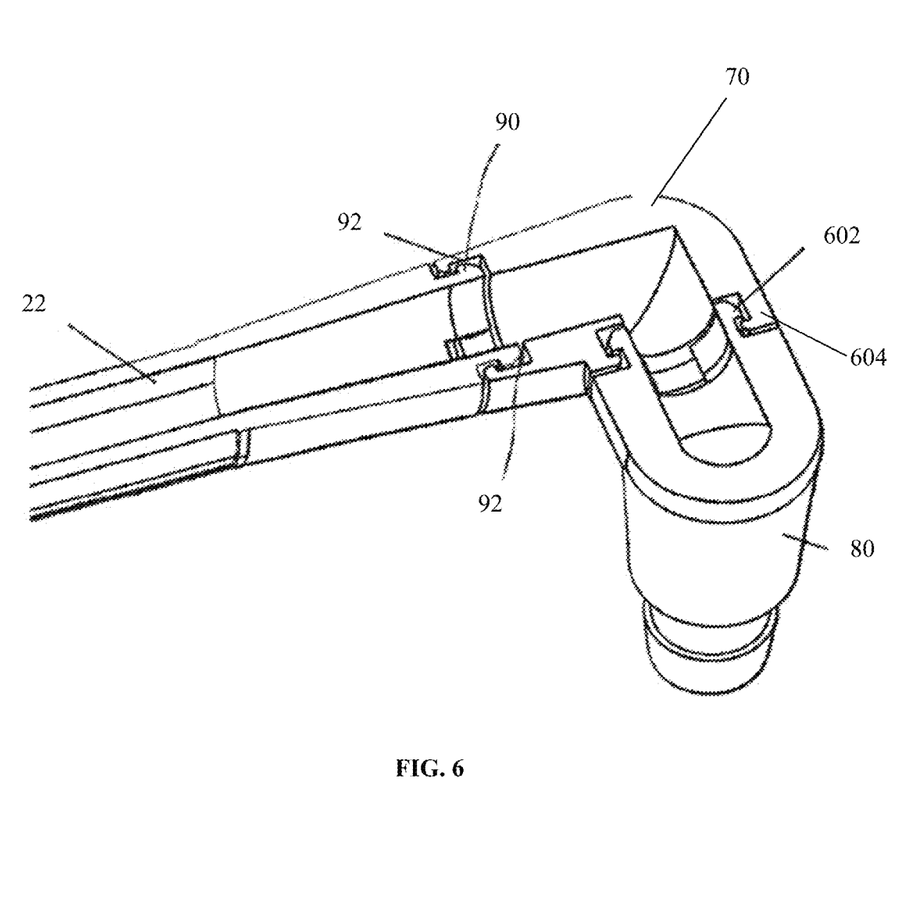
FIG. 6 is a perspective cross-sectional view of a second embodiment of a device suitable for use in practicing exemplary embodiments of this disclosure.

In FIG. 6, shown is a cross-sectional view of the swivel to body connection and swivel to hose connection are shown in detail. The body 22 may be formed with a projection 90 that fits into a slot 92 formed in the swivel portion 70. The engagement of the projection 90 with the slot 92 allows for rotation between the parts but maintains the coupling of the two parts. The hose connection 80 includes a projection 602 coupled to hose connection 80 that fits into a slot 604 formed in the swivel portion 70. Other mechanical means for joining the parts but allowing rotation of the swivel portion relative to the body will be evident to persons of ordinary skill in the art based on this disclosure.

Figure 7A:
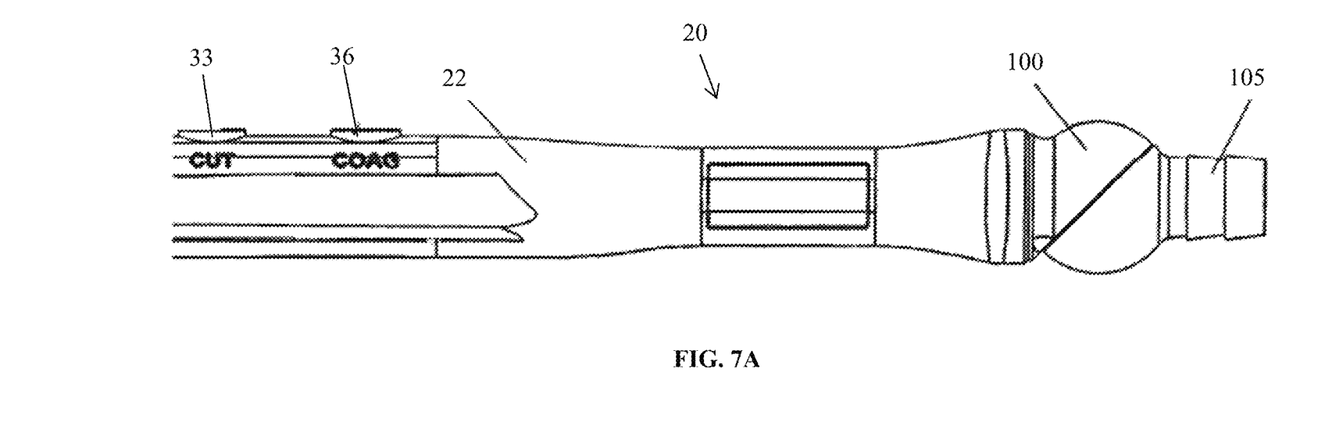
FIG. 7A is a side elevation view of a third embodiment of a device suitable for use in practicing exemplary embodiments of this disclosure.
Figure 7B:
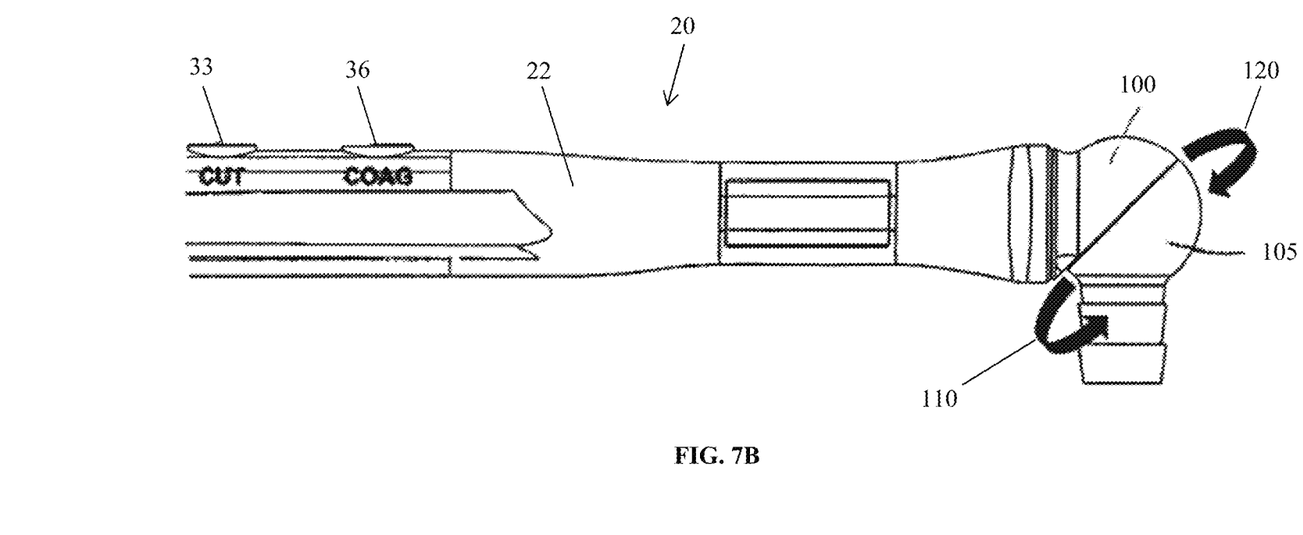
FIG. 7B is a side elevation view of the third embodiment of a device suitable for use in practicing exemplary embodiments of this disclosure.

Turning to FIGS. 7A and 7B, in another embodiment a swivel portion 100 may be attached at an angle to a hose connector 105. The hose connector 105 is connected to the swivel portion 100 at an approximately forty-five degree angle. However, it should be appreciated that embodiments include the hose connector 105 being connected to the swivel portion 100 between approximately 0 degrees to 45 degrees. The angle allows the hose connection to be pointed straight back (FIG. 7A), collinear to the pen body 22, perpendicular to the pen body 22 (FIG. 7B), or any angle in between. While a forty-five degree angle is shown, the angle may increase or decrease to allow for a different range of movement. The hose connector 105 may rotate in the direction of arrows 110 and 120.

Figure 8:
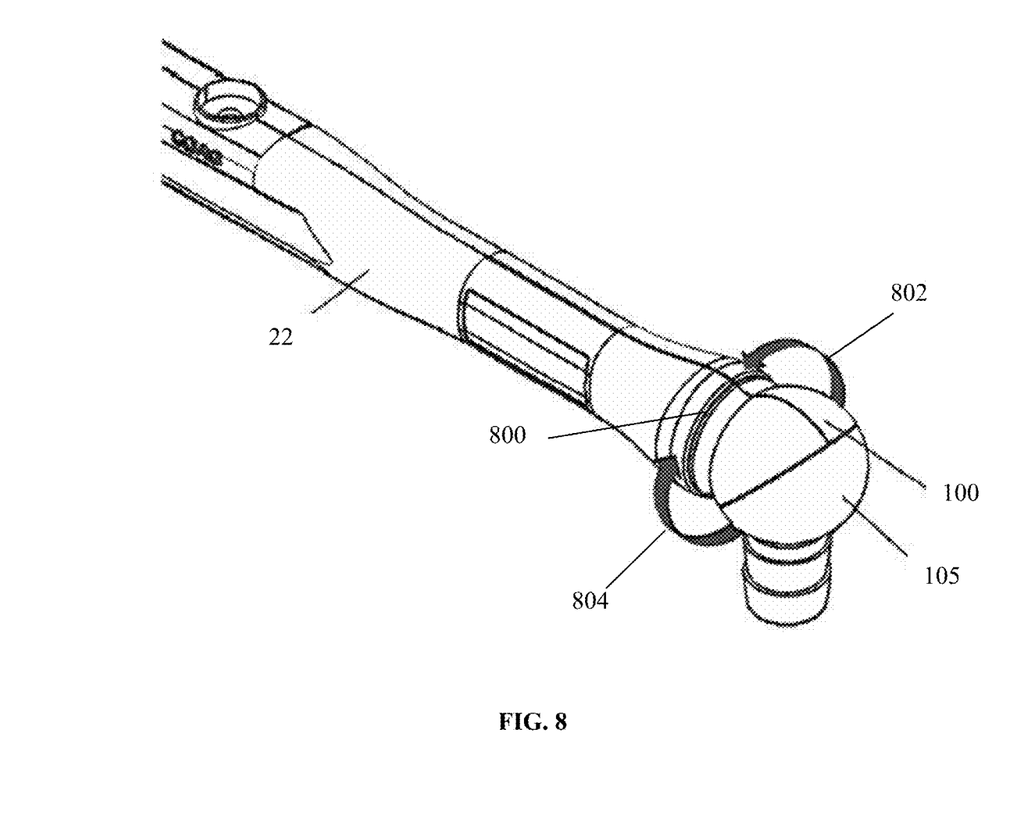
FIG. 8 is a perspective view of the third embodiment of a device suitable for use in practicing exemplary embodiments of this disclosure.

Turning to FIG. 8, a second pivot point 800 may be located between the body and the swivel portion. The swivel portion is connected to the body as disclosed in FIG. 3 discussed above and may rotate about the longitudinal axis of the body as illustrated by arrows 802, 804.

Figure 9:
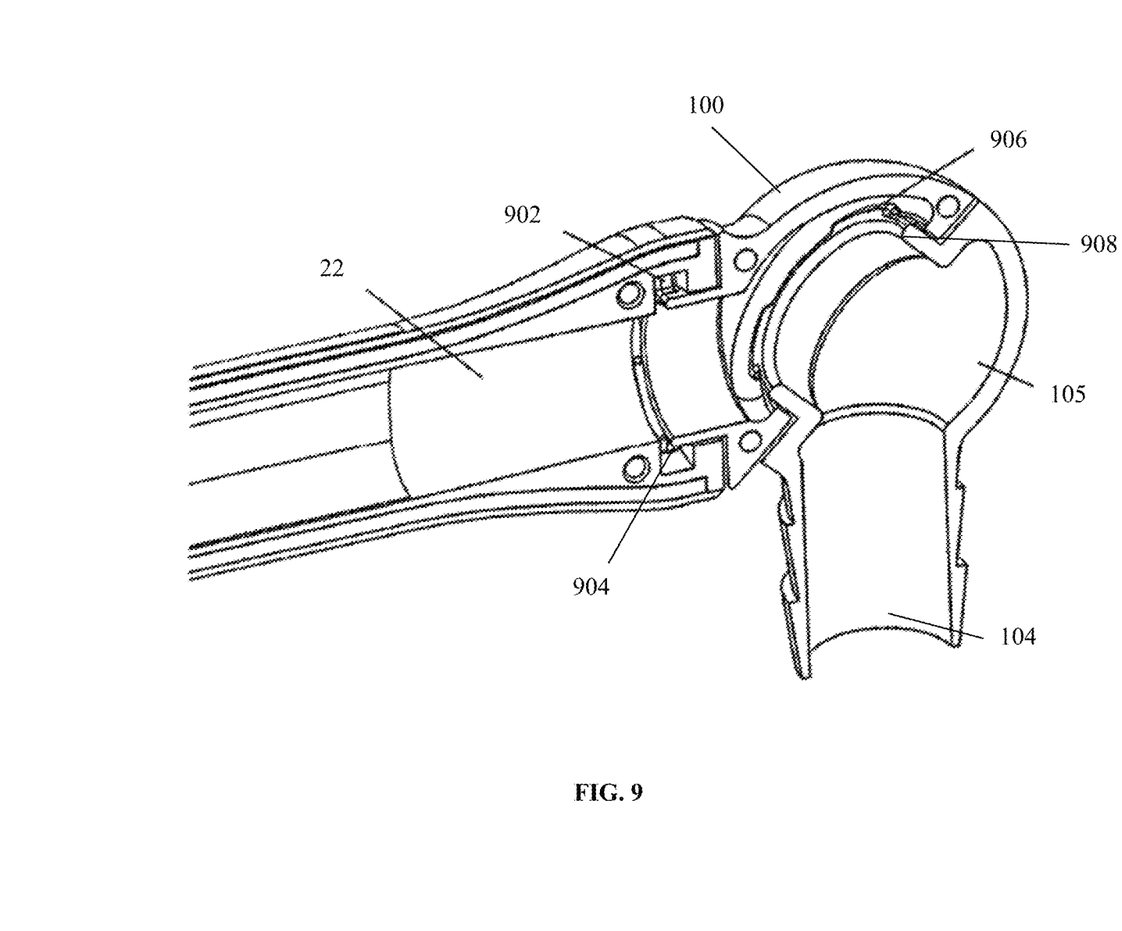
FIG. 9 is a partial cross-sectional view of a portion of the third embodiment of a device suitable for use in practicing exemplary embodiments of this disclosure.

Turning to FIG. 9, shown is a cross-sectional view of the embodiment shown in FIG. 8 depicting the swivel 100 to body 22 connection and the swivel 100 to hose 105 connection. The swivel 100 to body 22 connection is similar to the connection shown and described in FIG. 3 with a projection 904 extending into a corresponding slot 902 allowing for rotation of swivel 100 relative to body 22. Illustrated in FIG. 9 is the swivel 100 to hose 105 connection at a forty five degree angle. The connection between swivel 100 and hose 105 uses a projection 908 and a corresponding slot 906 that provides for rotation but does not allow the parts to separate. In other embodiments, each of the swivel 100 to body 22 connection and the swivel 100 to hose 105 connection may be set at alternative angles. For example, the swivel 100 to body 22 connection may be at a twenty degree angle while the swivel 100 to hose 105 connection may be at a ninety degree angle. A barbed fitting 28 is disposed on the outlet 104 of the hose 105 connection.

Figure 10:
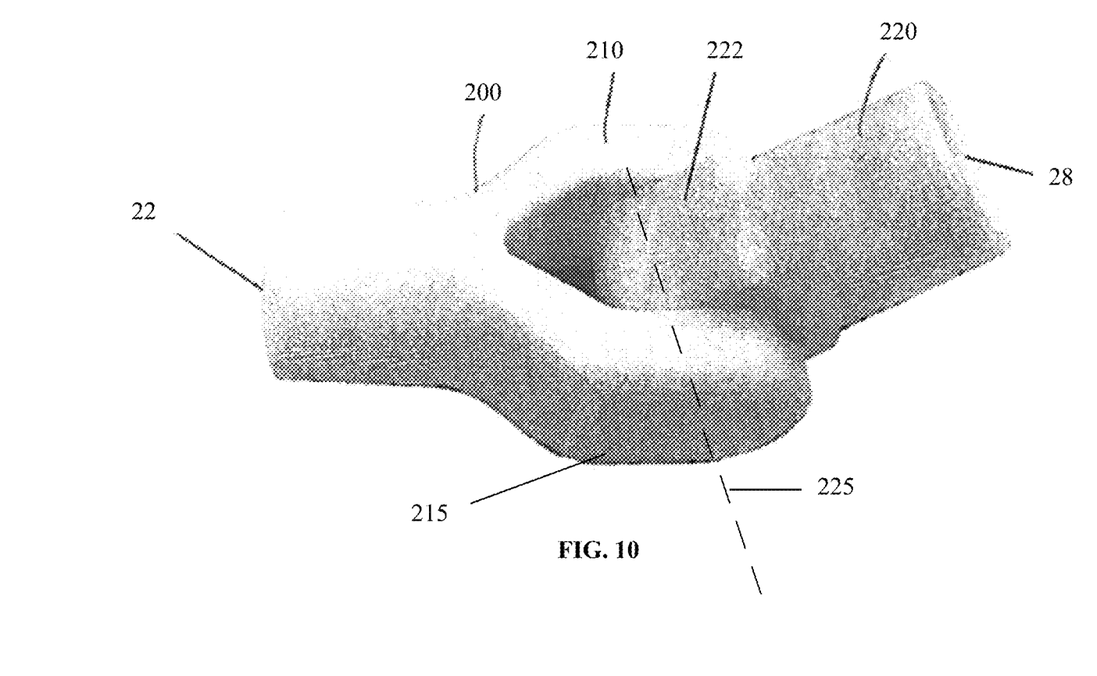
FIG. 10 is a perspective view of a fourth embodiment of a device suitable for use practicing exemplary embodiments of this disclosure.

In FIG. 10, another embodiment of the invention includes a swivel portion 200 having a pair of arms 210 and 215 that extend parallel to each other. A hose connection 220 is pivotally attached to the swivel portion 200 by means of a pivot pin 222 extending between the arms 210, 215. The hose connection 220 has an opening for receiving the pivot pin 222. The swivel portion 200 and the arms 210 and 215 are all hollow such that air from the passageway 302 passes through the body 22 and into the swivel portion 200. From the swivel portion 200, the air flows into the hose 220 connector through a hollow pivot pin 222. The air then exits through the center of the hose connector 220.

This disclosure has been described in detail with particular reference to an embodiment, but it will be understood that variations and modifications can be effected within the spirit and scope of the disclosure. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. An apparatus for surgical procedures, the apparatus comprising:
an electrode extending from a distal end of the body adjacent to an inlet;
a body having a longitudinal axis, the body comprising a hollow passageway extending through the longitudinal axis from the inlet to a port, the port comprising a first slot located on an inner wall of the hollow passageway;
a first button disposed on the body spaced relative to the inlet, the first button operable to control a current flow to the electrode; and
a swivel portion comprising a swivel and a hose connector, the swivel comprising a first projection located at a first opening and a second slot located at a second opening, the first projection operable to interface with the first slot, wherein the swivel is rotatably moveably coupled to the port, the second slot located on an inner wall of the swivel circumscribing the second opening, the hose connector comprising a second projection and an outlet, the swivel portion having a second hollow passageway fluidly coupled to the hollow passageway extending from the port to the outlet, wherein the swivel is operable to rotate around the longitudinal axis relative to the body, and wherein the second projection is operable to interface with the second slot such that an angle between the longitudinal axis of the body and the second projection is between 0 degrees to 45 degrees, wherein the hose connector is operable to rotate independent of the body and the swivel, and wherein the rotation of the hose connector within the second slot about an axis normal to the second opening is configured to cause an angle between a longitudinal axis of the hose connector and the longitudinal axis of the body to vary from 0 degrees to 90 degrees.

2. The apparatus according to claim 1, wherein the outlet is operable to be removeably attached to a vacuum tube and a vacuum.

3. The apparatus according to claim 1, the apparatus further comprising a second button on the body spaced relative to the inlet, the second button operable to control a current flow to the electrode.

4. The apparatus according to claim 3, wherein the first button is operable to activate the electrode at a first power level, the second electrode is operable to activate the electrode at a second power level, and wherein the first power level is different from the second power level.

5. An electrosurgical device, the electrosurgical device comprising:
a body having a longitudinal axis, the body comprising a hollow passageway extending through the longitudinal axis from an inlet at a distal end to a port at a proximal end;
an electrode extending from the distal end of the body adjacent to the inlet;
a first button disposed on the body spaced relative to the inlet, the first button operable to control a current flow to the electrode; and
a swivel portion moveably coupled to the port, the swivel portion having a second hollow passageway fluidly coupled to the hollow passageway extending from the port to an outlet, wherein the swivel portion comprises a first swivel element and a second swivel element, the first swivel element operable to rotate around the longitudinal axis relative to the body, wherein an interface between the first swivel element and the second swivel element are such that an angle between the longitudinal axis of the body and a longitudinal axis of the hose connector is between 0 degrees and 45 degrees, wherein the interface between the first swivel element and the second swivel element circumscribes the second hollow passageway, the second swivel element operable to rotate relative to the first swivel element and the body about an axis normal to the interface, wherein the second swivel element is configured to rotate independent of the body and the first swivel element about an axis normal to the interface causing an angle between a longitudinal axis of the hose connector and the longitudinal axis of the body to vary from 0 degrees to 90 degrees.

6. The electrosurgical device according to claim 5, wherein the first swivel element comprises a curved portion angled between 45 degrees and 90 degrees relative to the longitudinal axis.

7. The electrosurgical device according to claim 5, wherein the outlet is operable to be removeably attached to a vacuum tube and a vacuum, and wherein the body with the hollow passageway and the swivel portion with the second hollow passageway with the vacuum and vacuum tube are operable to evacuate surgical smoke from a cavity there through.

8. The electrosurgical device according to claim 5, the electrosurgical device further comprising a second button on the body spaced relative to the inlet, the second button operable to control a current flow to the electrode.

9. A method comprising:
(a) providing a body having a longitudinal axis, the body comprising a hollow passageway extending through the longitudinal axis from an inlet at a distal end to a port at a proximal end;
(b) providing an electrode extending from the distal end of the body adjacent to the inlet;
(c) providing a first button disposed on the body spaced relative to the inlet, the first button operable to control a current flow to the electrode; and
(d) providing a swivel portion moveably coupled to the port, the swivel portion having a second hollow passageway fluidly coupled to the hollow passageway extending from the port to an outlet, wherein the swivel portion comprises a first swivel element and a second swivel element, the first swivel element operable to rotate around the longitudinal axis relative to the body, wherein an interface between the first swivel element and the second swivel element is such that an angle between the longitudinal axis of the body and a longitudinal axis of the hose connector is between 0 degrees and 45 degrees, wherein the interface between the first swivel element and the second swivel element circumscribes the second hollow passageway, the second swivel element operable to rotate relative to the first swivel element and the body, wherein the second swivel element is configured to rotate independent of the body about an axis normal to the interface causing an angle between a longitudinal axis of the hose connector and a longitudinal axis of the body to vary from 0 degrees to between 45 degrees.

10. The method according to claim 9, wherein the first swivel element comprises a curved portion angled between 45 degrees and 90 degrees relative to the longitudinal axis.

11. The method according to claim 9, wherein the outlet is operable to be removeably attached to a vacuum tube and a vacuum.

12. The method according to claim 9, the electrosurgical device further comprising a second button on the body spaced relative to the inlet, the second button operable to control a current flow to the electrode.

\* \* \* \* \*